(12) United States Patent
Mizutani

(10) Patent No.: US 6,413,248 B1
(45) Date of Patent: *Jul. 2, 2002

(54) SANITARY NAPKIN

(75) Inventor: Satoshi Mizutani, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/332,636

(22) Filed: Jun. 9, 1999

(30) Foreign Application Priority Data

Jun. 12, 1998 (JP) .......................................... 10-165582

(51) Int. Cl.⁷ ............................................... A61F 13/15
(52) U.S. Cl. ............................. 604/385.17; 604/385.24
(58) Field of Search ........................ 604/385.01, 385.17, 604/385.24, 385.26, 385.27, 385.31

(56) References Cited

U.S. PATENT DOCUMENTS

| 4,595,392 A | * | 6/1986 | Johnson et al. | ......... 604/385.17 |
| 4,758,240 A | | 7/1988 | Glassman | |
| 4,804,380 A | * | 2/1989 | Lassen et al. | .......... 604/385.01 |
| 5,127,911 A | * | 7/1992 | Baharav | ................ 604/385.01 |
| 5,683,374 A | | 11/1997 | Yamamoto et al. | |
| 6,042,575 A | * | 3/2000 | Osborn, III et al. | .... 604/385.17 |

FOREIGN PATENT DOCUMENTS

| EP | 0 136 524 | | 4/1985 | |
| EP | 0 904 755 A2 | | 3/1999 | |
| GB | 2 282 522 A | | 4/1995 | |
| GB | 2 296 437 A | | 7/1996 | |
| JP | A-2-11138 | | 1/1990 | |
| JP | B-2744048 | | 2/1998 | |
| WO | WO 95/17148 | * | 6/1995 | ............ 604/385.17 |
| WO | WO 97/07763 | | 3/1997 | |
| WO | WO 98/37840 | | 9/1998 | |

OTHER PUBLICATIONS

Copy of European Search Report mailed Feb. 1, 2001.

* cited by examiner

Primary Examiner—Dennis Ruhl
(74) Attorney, Agent, or Firm—Baker & Daniels

(57) ABSTRACT

A sanitary napkin includes an absorbent core, the core being bent substantially in an inverted V-shape along a first groove provided on a lower side of the core in its transverse middle and along a pair of second grooves provided on an upper side of the core along its side edges so as to form a protuberant region being convex toward a body side of the napkin. The core is provided on its lower side with a plurality of elastic members obliquely extending across the first groove and secured to the core under tension. The napkin thus constructed does not create a feeling of discomfort against a wearer.

5 Claims, 4 Drawing Sheets

SANITARY NAPKIN

BACKGROUND OF THE INVENTION

This invention relates to a sanitary napkin for absorbing and containing menstrual fluids.

Japanese Patent Gazette No. 2744048 discloses a sanitary napkin being convex toward a wearer's body side and including elastic means extending transversely across an absorbent element. The elastic means is secured under tension to the napkin at two or more points thereon.

Japanese Patent Application Disclosure Gazette (Kokai) No. Hei2-11138 describes a sanitary napkin adapted to be curved convexly upward as the napkin is put on a wearer's body and including an absorbent core which is provided all over its lower side with a deformation element having a high bending stiffness. The deformation element may be provided, for example, in the form of moldings of polyethylene foam.

The sanitary napkin disclosed in the Japanese Patent Gazette No. 2744048 is disadvantageous in that the convex shape obtained by the elastic means depends on the individual sanitary napkins and is hardly uniformed in a predetermined shape. Most of the absorbent element principally comprise pulp fibers or a mixture of such pulp fibers and superabsorptive polymer particles. Such absorbent element has not necessarily an inter-fiber structure and a rigidity which are suitable for describing the convex shape. In addition, such absorbent element is often uneven in its density and therefore it can not be ensured that a substantially uniform convex shape is described.

The sanitary napkin described in the Japanese Patent Application Disclosure Gazette (Kokai) No. Hei2-11138 certainly makes it possible to obtain the uniform convex shape using the deformation element. However, the presence of the deformation element inevitably makes the napkin relatively bulky and this may create a feeling of discomfort against a wearer.

SUMMARY OF THE INVENTION

It is an object of the present invention to provide a sanitary napkin in which a protuberant region on an upper side of an absorbent core can be uniform in a predetermined shape without making the napkin bulky.

According to the present invention, there is provided a sanitary napkin comprising a liquid-pervious topsheet, a liquid-impervious backsheet and a liquid-absorbent core disposed therebetween, the sanitary napkin having a contour defined by first and second ends extending in a transverse direction of the napkin and first and second side edges extending continuously from the first and second ends, respectively, in a longitudinal direction of the napkin, the core being formed in a transverse middle thereof with a protuberant region convexly curved toward a body side of the napkin.

In such sanitary napkin, the present invention is characterized by that the protuberant region is formed by bending the core substantially in an inverted V-shape along a first groove extending substantially in alignment with a center line dividing the core in two transversely thereof and being concave from a lower side toward an upper side of the core, and along a pair of second grooves extending in the longitudinal direction in vicinities of the side edges of the core and being concave from the upper side toward the lower side of the core, and the core is provided on the lower side thereof with a plurality of elastic members secured thereto under tension and obliquely extending across the first groove.

According to one embodiment of the present invention, the plurality of elastic members intersect each other.

According to another embodiment of the present invention, the plurality of elastic members intersect the first groove at an angle in a range of 20~70°.

According to still another embodiment of the present invention, the core is provided on the lower side thereof with a hydrophobic panel adapted to be bent in an inverted V-shape substantially in conformity with the inverted V-shape of the core.

According to further another embodiment of the present invention, at least one of the plurality of elastic members extends in parallel to the center line of the core under tension between a longitudinal middle of said napkin and the first end and/or the longitudinal middle and the second end, and the napkin is folded with the topsheet lying inside along an imaginary line or imaginary lines extending transversely of the napkin orthogonally to sections of the elastic member(s) extending in parallel to the center line so that the napkin is packaged in such a folded state.

DETAILED DESCRIPTION OF THE PREFERRED EMBODIMENTS

Details of a sanitary napkin according to the present invention will be more fully understood from the description given hereunder with reference to the accompanying drawings.

Figure 1:
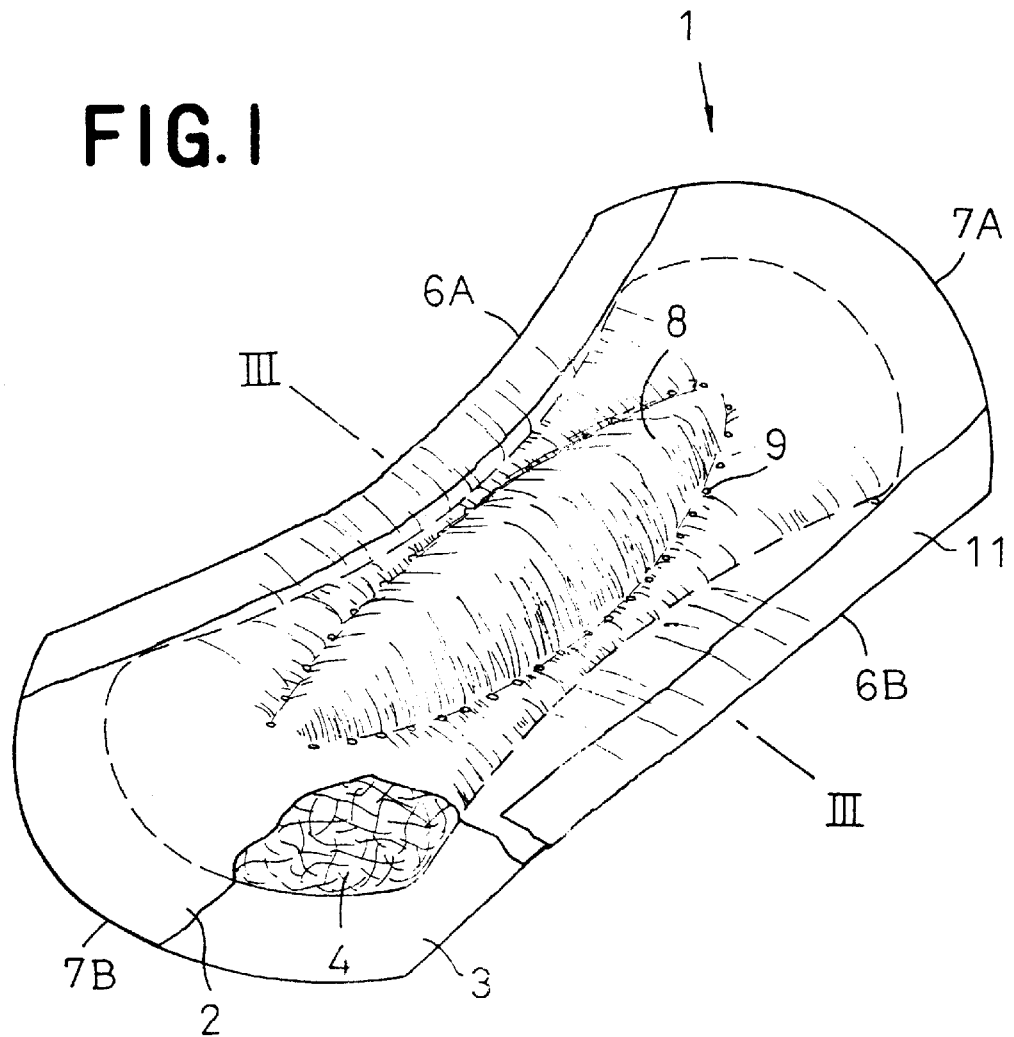
FIG. 1 is a perspective view showing a sanitary napkin according to one embodiment of the present invention as partially broken away.

A sanitary napkin 1 shown by FIG. 1 in a perspective view as partially broken away comprises a liquid-pervious topsheet 2, a liquid-impervious backsheet 3 and a liquid-absorbent core 4 disposed between these two sheets 2, 3. The napkin 1 has a contour defined by first and second side edges 6A, 6B extending in parallel to each other in a longitudinal direction and first and second ends 7A, 7B extending in parallel to each other in a transverse direction so as to intersect the side edges 6A, 6B. The topsheet 2 and the backsheet 3 extend outward beyond a periphery of the core 4 and are placed upon and bonded together along their respective extensions. The napkin 1 is formed in its transversely middle with a protuberant region 8 curved convexly from the lower side toward the upper side of the napkin 1. This protuberant region 8 longitudinally extends toward the first and second ends 7A, 7B. The napkin 1 is formed on its upper side with a pair of second compressed zones 9, 9 each extending longitudinally of the protuberant region 8 intermittently or continuously along a base of the protuberant region 8. In each of the second compressed zones 9, 9, the upper side of the napkin 1 sinks. A pair of elastically stretchable/contractable sheets 11, 11 are bonded to the napkin 1 respectively along the first and second side edges 6A, 6B under longitudinal tension. These sheets 11, 11 are folded back onto the lower side of the napkin 1 respectively along the side edges 6A, 6B. Contraction of these sheets 11, 11 cause the napkin 1 to be slightly curved inward with the topsheet 2 lying inside between its opposite ends 7A, 7B.

Figure 3:
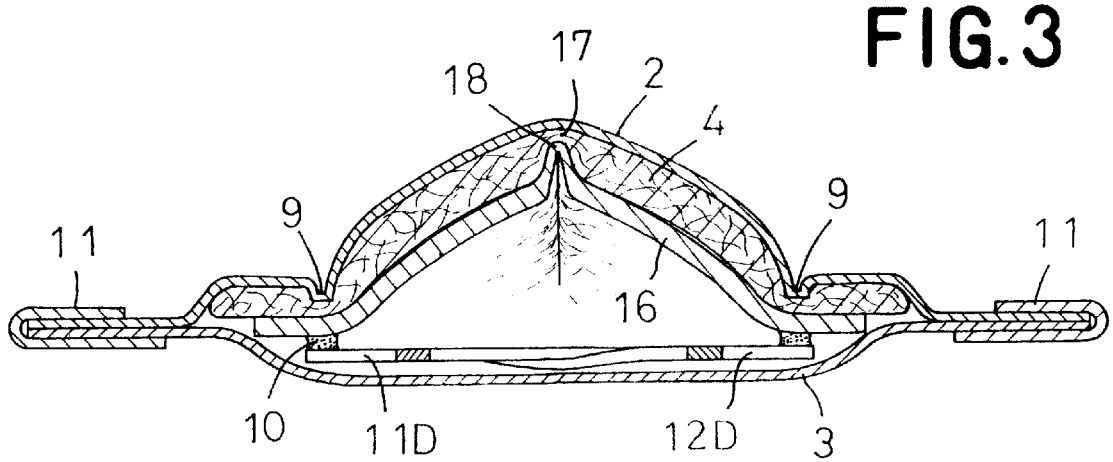
FIG. 3 is a sectional view taken along a line III—III in FIG. 1.
Figure 2:
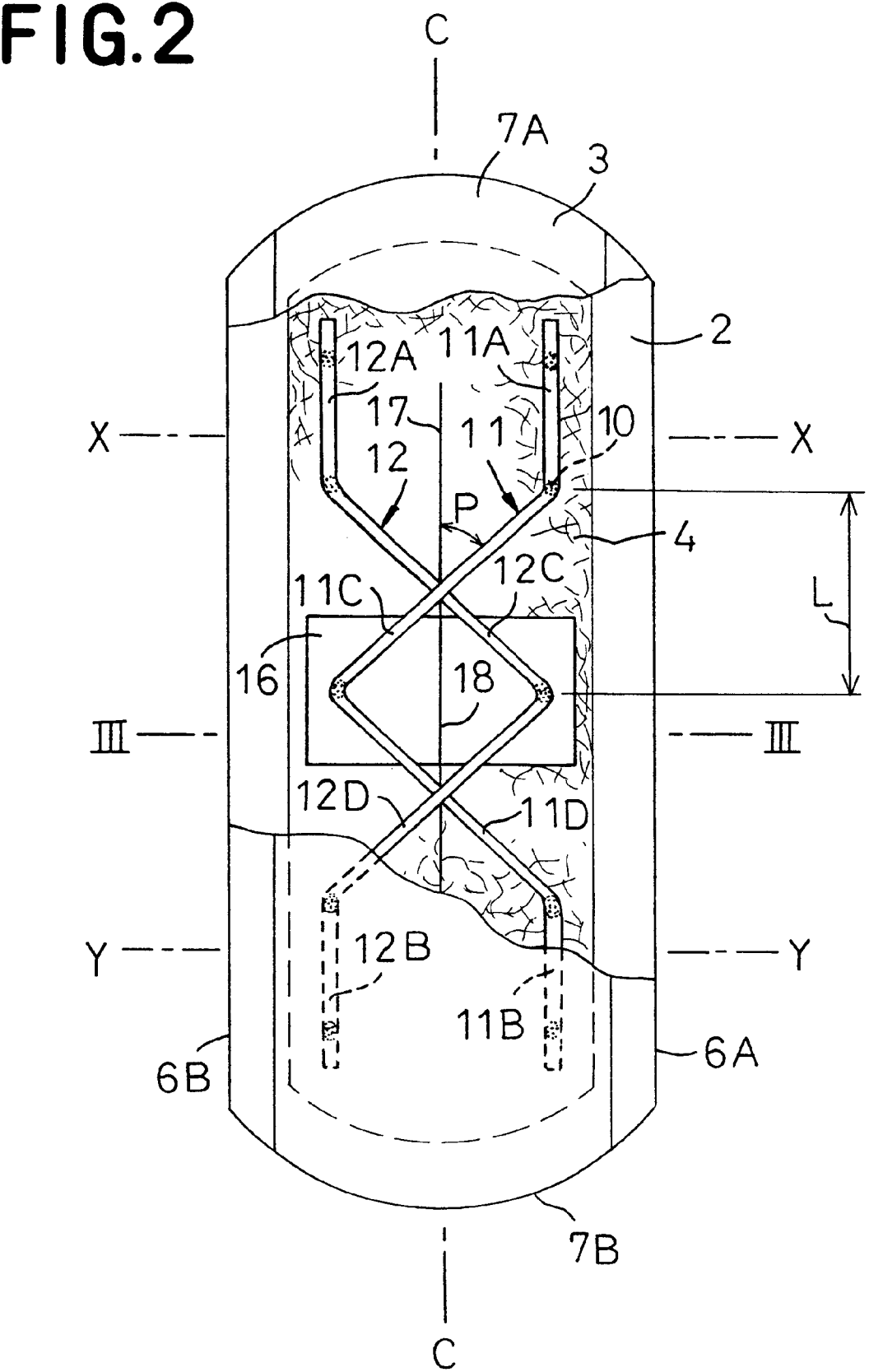
FIG. 2 is a plan view showing a lower side of the napkin as partially broken away.

FIG. 2 is a plan view showing the lower side of the napkin as partially broken away and FIG. 3 is a sectional view taken along a line III—III in FIGS. 1 and 2. Referring to FIGS. 2 and 3, the napkin 1 is provided symmetrically with respect to a center line C—C transversely dividing the napkin 1 in two with first and second elastic members 11, 12 each being secured under a tension to the napkin 1. As will be apparent from FIG. 2, the first and second elastic members 11, 12 are secured to the lower surface of the core 4 by means of hot melt adhesive 10 and have first and second rectilinear sections 11A, 12A; 11B, 12B longitudinally extending in parallel to the center line C—C in the vicinities of the first and second ends 7A, 7B, respectively. Between the first rectilinear sections 11A, 12A and the second rectilinear sections 11B,, 12B, the respective elastic members 11, 12 have first and second rectilinear intermediate sections 11C 12C; 11D, 12D, obliquely intersecting the center line C—C. Specifically to describe the case of the first elastic member 11, the first rectilinear intermediate section 11C obliquely extends from the vicinity of the first side edge 6A across the center line C—C to the vicinity of the second side edge 6B. The second rectilinear intermediate section obliquely extends from the vicinity of the second side edge 6B across the center line C—C to the vicinity of the first side edge 6A. A manner in which the first and second rectilinear intermediate sections 12C, 12D of the second elastic member 12 extend is similar to the manner in which the first elastic member 11 extends.

The core 4 is compressed in a direction from its lower side toward its upper side to form, on its lower side in its transverse middle, a first compressed zone 17 intermittently or continuously extending in parallel to the center line C—C. In the longitudinal middle, the core 4 is provided on its lower side with a hydrophobic panel 16 preferably made of thermoplastic synthetic fibers extending transversely of the core 4 across the first compressed zone 17. The panel 16 is formed on its lower side with a compressed zone 18 similar to the first compressed zone 17.

With such an arrangement, contraction of the first and second elastic members 11, 12 causes the core 4 to be deformed along the first and second compressed zones 17, 9 so that the core 4 may form together with the topsheet 2 the protuberant region 8. It is also possible to form the core 4 substantially in a shape of the protuberant region 8 already when the first and second compressed zones 17, 9 are formed.

To obtain the napkin 1 as has been described above, a nonwoven fabric made of thermoplastic synthetic fibers or an apertured film made of thermoplastic synthetic resin may be employed as material for the topsheet 2. A film of thermoplastic synthetic resin may be employed as material for the backsheet. The liquid-absorbent core 4 may be formed by pulp fibers, a mixture of pulp fibers and superabsorptive polymer particles, or any one of the pulp fibers and superabsorptive polymer particles which contains 20% or less by weight of thermoplastic synthetic fibers. Since the napkin 1 comprises such materials, the first and second compressed zones 17, 9 can be formed by heat-sealing the thermoplastic materials with each other.

According to this embodiment, the first and second elastic members 11, 12 extending across the center-line C—C make the napkin 1 contractile in its transverse direction and thereby ensure a shape-holding effect for the protuberant region 8. The first rectilinear intermediate sections 11C and 12C of the first and second elastic members 11, 12, for example, can make the napkin 1 contractile over an extent L (See FIG. 2) defined longitudinally thereof. An angle P at which the first and second elastic members 11, 12 intersect the center line C—C is preferably selected in a range of 20~70°. While it may be contemplated to replace the first and second elastic members 11, 12 according to the present invention by a relatively large elastic sheet applied on the napkin 1 over the extent L, such replacement is inexpedient primarily from the viewpoint of a quantity by which the elastic material should be used. The larger the extent L is, the more significant an inexpediency of such replacement will be. It may be also contemplated to replace the first and second elastic members 11, 12 by a plurality of elastic ribbons extending in parallel one to another transversely of the core 4. However, such replacement is also inexpedient in view of various factors such as a productivity of the napkin and a quantity of elastic material which must be used, because the number of ribbons should be increased in order to enlarge the extent L.

It is now supposed that the napkin 1 according to the present invention is packaged in an individual envelope: Specifically, sections of the napkin 1 extending adjacent the first and second ends 7A, 7B, respectively, are folded back along first and second imaginary lines X—X, Y—Y extending orthogonally to the first and second rectilinear sections 11A, 12A; 11B, 12B, respectively, with the topsheet 2 lying inside. As the napkin 1 is taken out from the individual envelope, the first and second sections 11A, 12A, 11B, 12B of the elastic members 11, 12 contract and the folded sections restore their initial positions shown in FIG. 2. The napkin 1 packaged in this manner is easy to handle since neither time nor trouble of unfolding the napkin 1 once it has been taken out from the individual envelope. It is to be understood that stretch stresses of the first and second sections 11A, 12A, 11B, 12B in their positions shown in FIG. 2 should be large enough to unfold said sections of the napkin 1 but not to further deform the napkin 1.

The panel 16 functions to maintain the initial shape of the protuberant region 8 even when the core 4 has been wetted with body fluids and consequently its initial rigidity has been reduced. In order that the initial rigidity of the core 4 can be maintained even after body fluids have been discharged, hydrophobic material such as hydrophobic nonwoven fabric made of thermoplastic synthetic fiber or foamed plastic sheet may be employed as material for the panel 16. It should be understood that, depending on a composition of the core 4, use of such panel 16 can be eliminated.

Figure 4:
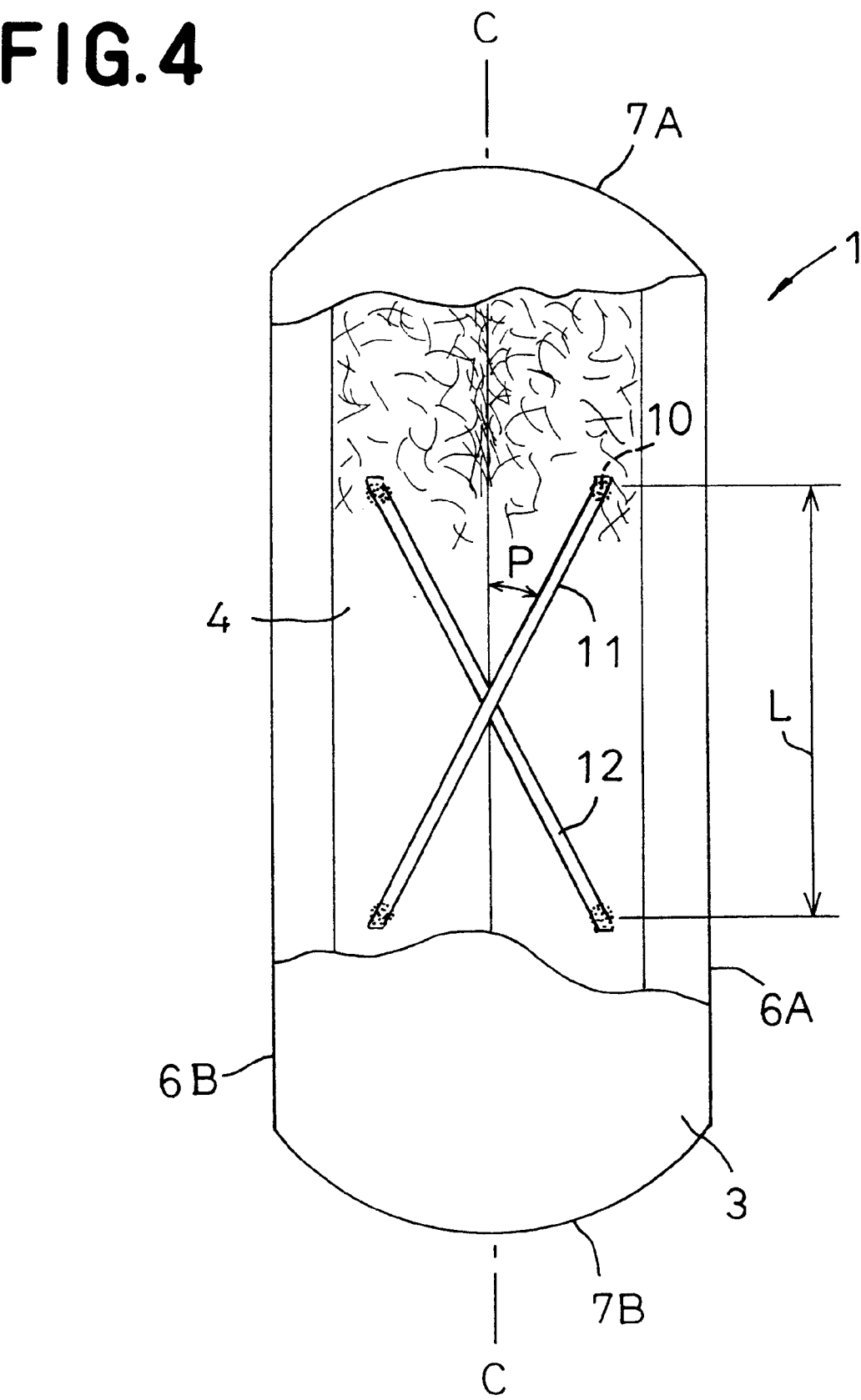
FIG. 4 is a view similar to FIG. 2, showing a sanitary napkin according to another embodiment of the present invention.

FIG. 4 is a view similar to FIG. 2, showing a sanitary napkin 1 according to another embodiment of the present invention. In the case of this napkin 1, the first elastic member 11 obliquely extends across the center line C—C in the longitudinally middle zone of the napkin 1 between the first side edge 6A and the second side edge 6B. The angle at which the first elastic member 11 intersects the center line C—C is in a range of 20~70°. The second elastic member 12 is arranged in a symmetrical relationship with the first elastic member 11 about the center line C—C. A contractile force in the transverse direction is normally exerted to the napkin 1 in its longitudinal extent L and in the vicinity of this extent L. The panel 16 is not adopted in this napkin 1.

Figure 5:
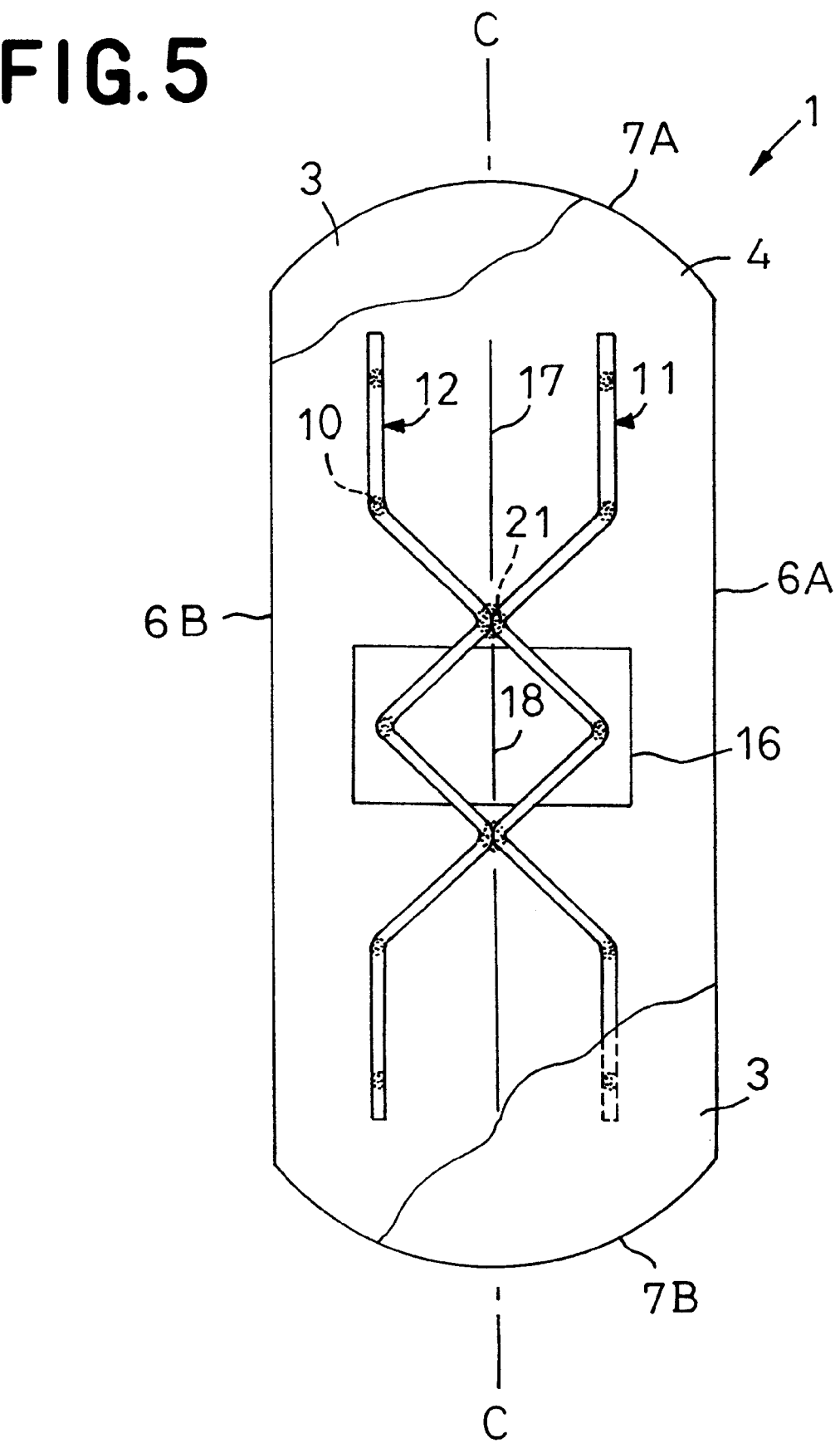
FIG. 5 is a view similar to FIG. 2, showing a sanitary napkin according to still another embodiment of the present invention.

FIG. 5 is a view similar to FIG. 2 showing a sanitary napkin 1 according to still another embodiment of the present invention. The first and second elastic members 11, 12 arranged in a symmetrical relationship with each other about the center line C—C obliquely extend from the vicinities of the respective side edges 6A, 6B to the center line C—C and are bonded to each other on said center line C—C by means of adhesive agent 21. While the respective elastic members 11, 12 do not extend across the center line C—C, a contractile force of these members 11, 12 is exerted on the napkin 1 across the center line C—C because these members 11, 12 are bonded to each other on the center line C—C.

The sanitary napkin according to the present invention effectively facilitates the protuberant region to be maintained in a predetermined shape since the protuberant region is formed along the guiding lines defined by the compressed recesses previously provided in desired zones on upper and lower sides of the napkin. The elastic members obliquely extend across the center line extending longitudinally of the napkin so that a relatively small quantity of such elastic members may be sufficient to hold the predetermined shape of the protuberant region over a large area of the napkin. Accordingly, there is no apprehension that the elastic members might make the napkin bulky and create a feeling of discomfort against a wearer.

What is claimed is:

1. A sanitary napkin comprising:

a liquid-pervious topsheet;

a liquid-impervious backsheet; and a liquid-absorbent core disposed between said liquid-pervious topsheet and said liquid-impervious backsheet, said sanitary napkin having a contour defined by first and second ends which extend in a transverse direction of said sanitary napkin and first and second side edges which extend continuously between said first and second ends, in a longitudinal direction of said sanitary napkin, said liquid-absorbent core being formed in a transverse middle portion thereof with a protuberant region convexly curved toward a body side of said sanitary napkin, said protuberant region being formed by bending said liquid-absorbent core substantially in an inverted V-shape along a first compressed zone which extends substantially in alignment with a longitudinal center line of said liquid-absorbent core and being concave from a lower side toward an upper side of said liquid-absorbent core, and by bending said liquid-absorbent core along a pair of second compressed zones which extend along said longitudinal direction in the vicinities of said side edges of said liquid-absorbent core and being concave from the upper side toward the lower side of said liquid-absorbent core, said liquid-absorbent core being provided on the lower side thereof with a plurality of elastic members bonded thereto under tension and obliquely extending across said first compressed zone.

2. The sanitary napkin according to claim 1, wherein said plurality of elastic members intersect each other.

3. The sanitary napkin according to claim 1, wherein said plurality of elastic members intersect said first compressed zone at an angle in a range of from about 20 to about 70°.

4. The sanitary napkin according to claim 1, wherein said liquid-absorbent core is provided on the lower side thereof with a hydrophobic panel adapted to be bent in an inverted V-shape substantially in conformity with the inverted V-shape of said liquid-absorbent core.

5. The sanitary napkin according to claim 1, wherein at least one of said plurality of elastic members extends in parallel to the center line of said liquid-absorbent core under tension between one of a longitudinal middle of said sanitary napkin and said first end, and said longitudinal middle and said second end, and said sanitary napkin is folded with said topsheet lying inside along at least one line extending transversely of said sanitary napkin orthogonally to sections of said elastic member(s) extending in parallel to said center line so that said sanitary napkin can be packaged in such a folded state.

* * * * *